United States Patent [19]

Prosl et al.

[11] Patent Number: 6,013,058
[45] Date of Patent: *Jan. 11, 2000

[54] DEVICE FOR SUBCUTANEOUS ACCESSIBILITY

[75] Inventors: Frank R. Prosl, Duxbury; Dale Whipple, East Taunton, both of Mass.

[73] Assignee: Biolink Corporation, Middleboro, Mass.

[*] Notice: This patent issued on a continued prosecution application filed under 37 CFR 1.53(d), and is subject to the twenty year patent term provisions of 35 U.S.C. 154(a)(2).

[21] Appl. No.: 08/661,903

[22] Filed: Jun. 12, 1996

[51] Int. Cl.[7] .................................................. A61M 5/178
[52] U.S. Cl. ........................ 604/167; 604/169; 604/247; 604/891.1; 128/DIG. 26; 128/912; 251/149.1
[58] Field of Search .............................. 604/93, 174, 175, 604/246, 283, 891.1, 167, 247, 256, 169, 264; 128/DIG. 26, 912; 251/149.1

[56] References Cited

U.S. PATENT DOCUMENTS

| | | |
|---|---|---|
| 4,566,493 | 1/1986 | Edwards et al. |
| 4,569,675 | 2/1986 | Prosl et al. .............................. 604/175 |
| 4,954,149 | 9/1990 | Fullemann ................................. 55/386 |
| 5,356,381 | 10/1994 | Ensminger et al. ...................... 604/93 |
| 5,460,616 | 10/1995 | Weinstein et al. ...................... 604/167 |
| 5,556,381 | 9/1996 | Ensminger et al. ...................... 604/93 |
| 5,556,385 | 9/1996 | Andersen ................................ 604/174 |
| 5,562,618 | 10/1996 | Cai et al. .................................. 604/93 |
| 5,704,915 | 1/1998 | Melsky et al. .......................... 604/284 |
| 5,738,664 | 4/1998 | Erskine et al. .......................... 604/256 |
| 5,782,817 | 7/1998 | Franzel et al. .......................... 604/256 |
| 5,911,706 | 6/1999 | Estabrook et al. ...................... 604/116 |

*Primary Examiner*—Wynn Wood Coggins
*Assistant Examiner*—LoAn H. Thanh
*Attorney, Agent, or Firm*—Perkins, Smith & Cohen, LLP; Edwin H. Paul; Jerry Cohen

[57] ABSTRACT

Hemodialysis access and lock device (10) and system, the device comprising an improved lock (32) formed of a resilient plug (34) surrounding an inserted needle cannula (NC) and having radial blades (40) with a tapered outer edge (42) locking to a corresponding tapered surface (44) of a surrounding shell (12) and an internal passage sealed by a duck-bill valve and a strain relief at a catheter and the system comprising one or more of such devices and corresponding hub structures (100) connectable to external fluid conduits and providing control of the needle cannula and an internal obturator (OB) associated with it.

26 Claims, 4 Drawing Sheets

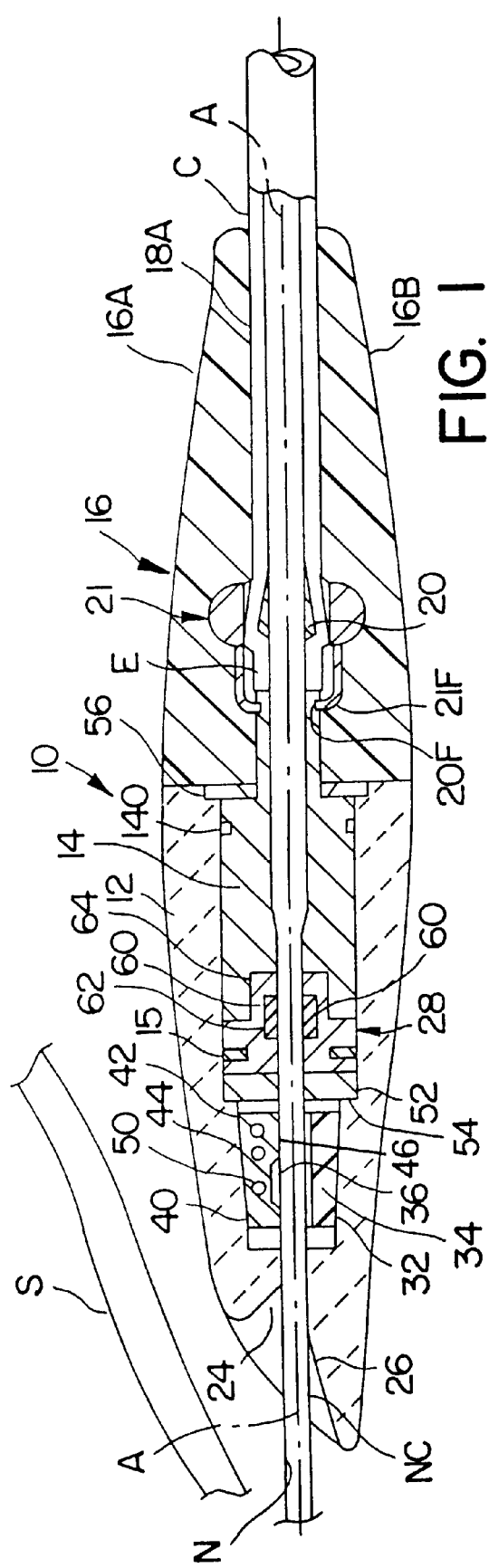
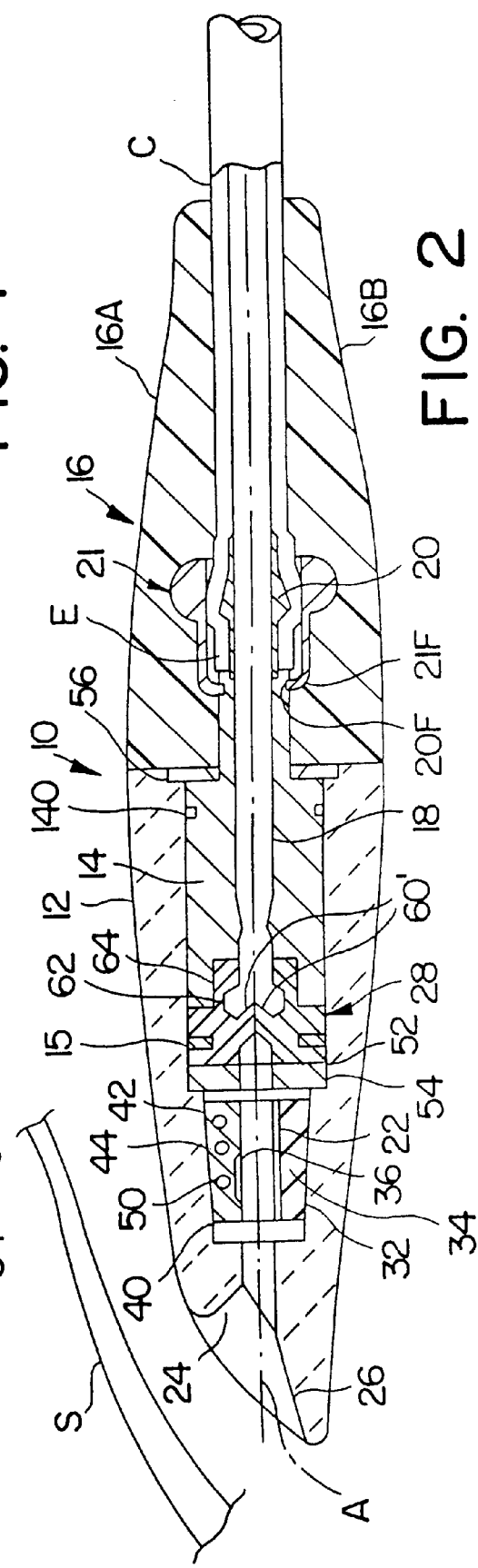
FIG. 1
FIG. 2

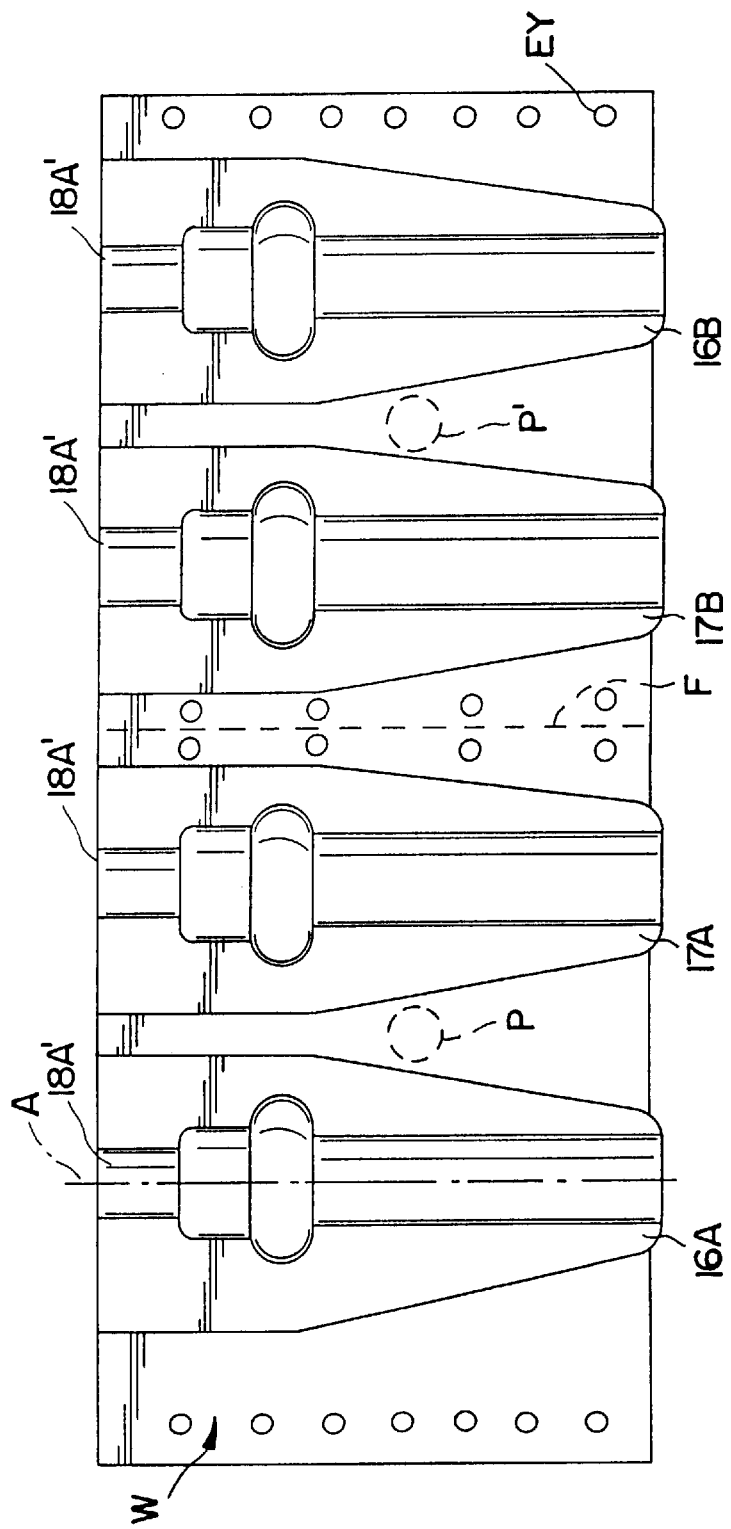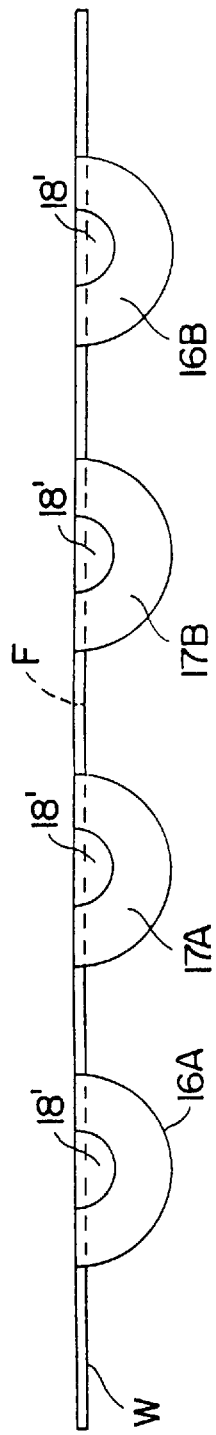

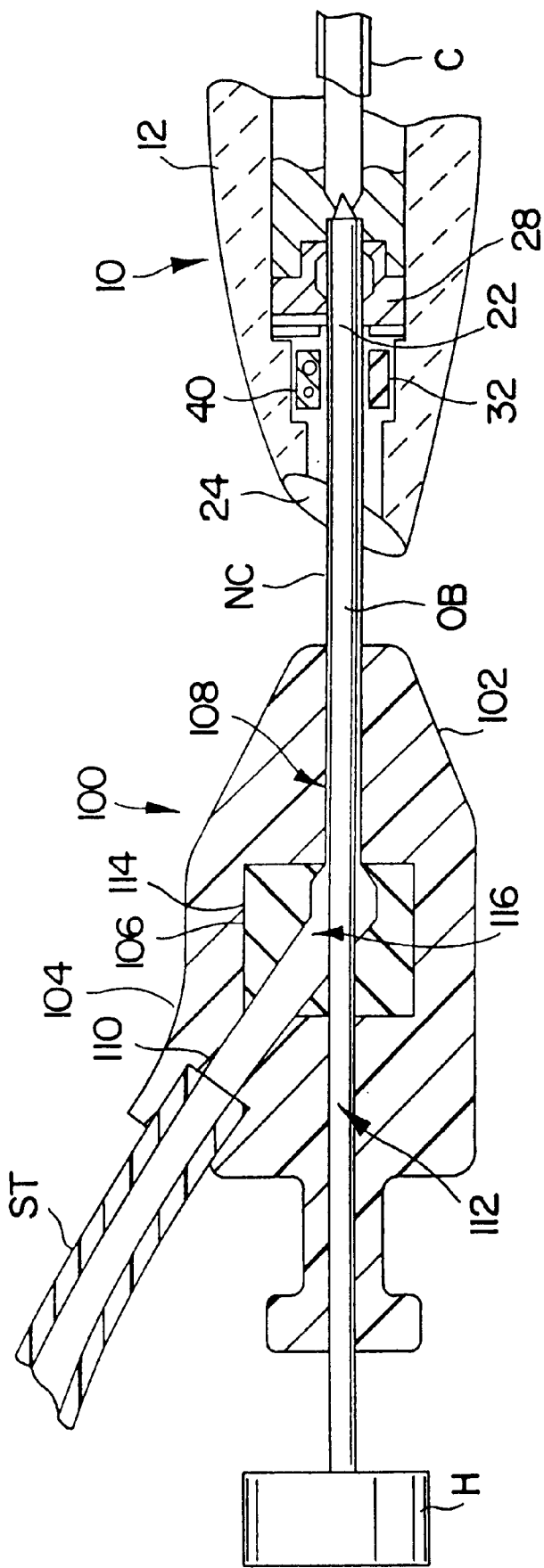
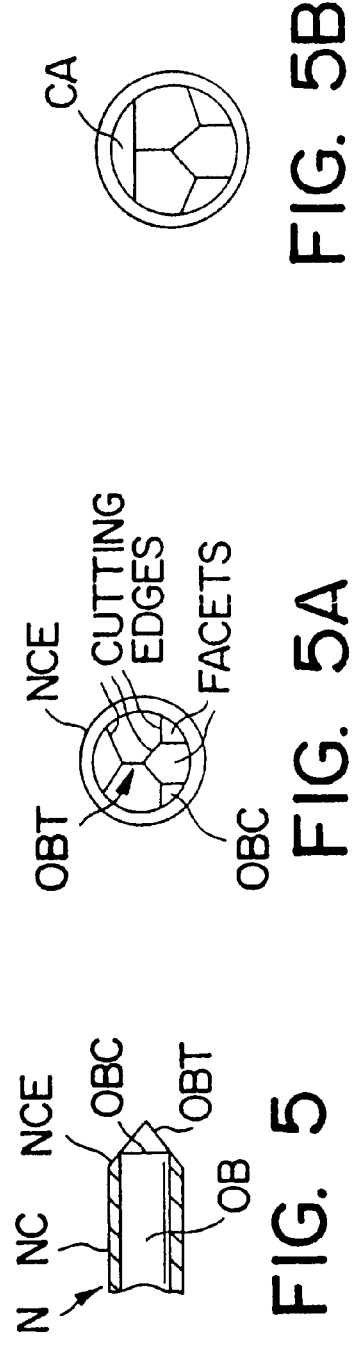
FIG. 4
FIG. 5
FIG. 5A
FIG. 5B

DEVICE FOR SUBCUTANEOUS ACCESSIBILITY

FIELD AND BACKGROUND OF THE INVENTION

The present invention relates to subcutaneous access and more particularly hemodialysis apparatus of the general type disclosed in copending U.S. patent applications of Frank Prosl, Ser. No. 08/485,498, filed Jun. 7, 1995 and Ser. No. 08/631,801, filed Apr. 11, 1996. The disclosures of said applications are incorporated herein by reference as though set out at length herein. The copending applications disclose and claim apparatus for assuring high flow rates for enhancing hemodialysis. Such apparatus includes a connected pair of catheter end attaching and cannula end locking devices (or a single such device or separate unconnected such devices) that is subcutaneously implanted. Each such device is arranged with an internal passage, one end of which can have a catheter proximal end attached thereto (the distal ends of the catheters of the two devices being at optimal regions of the patient for suction [e.g., atrium] and return [e.g., jugular vein] of blood). Each device or a connected pair of such devices is subcutaneously implanted and the other end of the internal passage of each device is just under the skin and easily accessed. A cannula (e.g. a hollow needle) or other conduit is locked into each device and used for blood flow between the device and external to the patient pumping/dialysis apparatus or other blood processing.

The present invention is also useful for other liquid transfer purposes in and out of human and animal bodies including transfer of externally prepared solutions for cleaning, flushing, dialysis, chemical agent delivery, transfusions, blood donation, insufflation, wound drainage, etc.

It is a principal object of the invention to optimize fluid flow in hemodialysis particularly and in other applications referred to generally, above.

It is a further object of the invention to enhance the devices to more effectively lock in a cannula to the device to avoid inadvertent separation, yet allow ease of deliberate release of the cannula.

It is a further object to the invention to minimize internal fluid collection zones in such a device.

It is a further object of the invention to provide ease of manufacture and assembly of such device consistent with enhanced locking.

It is a further object of the invention to minimize irritation and other adverse effects associated with intermittent skin puncture over a course of days, months or years of repetitive access.

A further object of the invention is to establish economy of the lock devices for disposability.

It is a further object of the invention to provide enhanced cannula and obturator handling external to a patient via hub devices coordinated with the structure and functions of the locking devices.

It is also an object of the invention to accommodate multiples of the foregoing objects together.

SUMMARY OF THE INVENTION

The objects of the invention are met by a ganged pair of implantable access devices or a single such device or separate such devices, each with a shell containing an internal passage with an entrance for receiving a cannula and an exit for transition connection to a catheter, a strain relief at the latter end and a cannula locking assembly within the device. A flexible seal is also provided within each device for shutting off flow through the internal passage of the device when the cannula is withdrawn. A strain relief wrap provided at the catheter attaching end of each device can also serve as a device anchor under the skin. Edges of the strain relief structure can be sutured or stapled to tissues and the strain relief wrap can in turn hold other portions of the device. The needle cannula or other conduit locked at a distal end into the device has its proximal end in a hub structure that provides a smooth flow path for blood feed.

The flexible lock preferably comprises a resilient plug (preferably made of a medical quality rubber or elastomer) surrounding an inserted hollow metal cannula, but containing rigid internal blades or strips (preferably made of hard material such as a hard ceramic or metal) that extend radially in locking use and are configured and arranged to inscribe the cannula surface or at least bear on it with a high reaction force. Thus, when an inadvertent pull on the needle from outside (or the push of a muscular contraction from within) places an expelling force on the needle, the beginning of movement increases the locking effect. The blades or strips have inner edges that form one or more teeth of pointed or blunt ends, such teeth having shallow clearance angles with respect to the passage axis. The blades have outer edges that are locked in geometrically by a tapered inner surface of the shell.

Deliberate removal can be done by rotating and/or wiggling (spiral or combination of axial/rotation movements) of the cannula so that the orientation of the blades shifts from essentially radial to essentially non-radial alignment relative to the device's internal passage axis. When the plug and blades are disposed non-radially the cannula can be withdrawn easily. The rotation or the like is then relaxed (after complete removal of the cannula) and the blades are restored to radial alignment by the elasticity of the plug.

When the needle is reinserted (typically one or more days later) the entering cannula passes through the inner edges of the blades. Generally there is a full withdrawal of a cannula or a full insertion; but partial insertion and/or withdrawals can also be accommodated.

The resilient plug body is set radially apart from the cannula surface to avoid shedding or uneven friction due to thermal conditions or other sources of expansion/contraction of the flexible plug (e.g. made of silicone rubber). The flexible plug material is preferably cast in a mold about the aligned (radial) blades. Holes or the equivalent are provided in the blades so that the flexible material on both sides of each blade is bridged via such holes or other means and the blades are securely aligned therein radially and with inner and outer edges of the blades extending beyond inner and outer plug surfaces. Generally, there is a low axial direction friction meeting of the blade outer edges and the tapered (frusto-conical) shell inner surface. A ceramic shell with a smooth finish inner tapered surface meets this criterion very well. Similarly the blade inner edges slide along the cannula outer surfaces with low friction. The hardness of all such surfaces and the rigidity and dimensional stability of blades, cannula and shell are related to the above features and also important per se.

The device also comprises a further duck-bill plug with spring loading of its two flaps to block the internal passage of the device when the cannula is withdrawn and yet is readily opened as the cannula is inserted without damage. The duck-bill valve is surrounded by a fill of inert, flexible material to minimize available volume for fluid. When the valve flaps are retracted, they expel blood from the volume. Similar valves can be applied with more than two flaps or lobes swinging through axial planes between opening and closing. Hybrids can also be designed. In any such design, it is preferable to have automatic spring loaded closing when the cannula is withdrawn and easy opening as a needle assembly or the like is inserted through the device's internal passage.

A series of seal means are also provided to deal with leakage paths that are otherwise conduits for infection or clotting problems or the like if not resolved.

Ease of use and foolproof reliability in the operative implantation setting are also accommodated by features discussed below.

The invention also includes an outside the body hub structure or pair of such structures usable in combination with the implanted subcutaneous device(s) for straight cannula alignment, and alignment of a cutter (a separate element or integrated with the cannula) that has to penetrate the skin, find the entrance to the inner passage of the subcutaneous device and pass through it to a lock-in site therein. The hub has a Y-connection of three internal paths: (a) external fluid passage, (b) passage to the cannula and (c) a cannula/cutter access leg, all cooperating with shallow bend angles and gradual radii of curvature at the Y-intersection in the fluid path and straight line access to the lock device for the needle assembly, as consistent with practical and economic mass production.

The needle is initially inserted through the hub structure (or comes preassembled with it) and has an internal obturator with a point that passes out of the needle distal end for penetrating skin and subcutaneous tissue and serving as an aid to finding the subcutaneous entrance to the access and lock device. The obturator end is faceted so that its cutting is done along meeting lines of facets but only over a very short length. However, when the obturator point goes through the passage, it does not cut, score or otherwise mar the internal wall of the passage or interiors of the locking and sealing components of the device which form part of the passage. The obturator point is followed by a collar section, extending out of the cannula end, that is also faceted but in a larger number of facets than in the region of the point and at a larger diameter, so that scoring of the internal passage of the device is avoided. The collar section of the obturator blends into a beveled end of the cannula. Once the needle is fully inserted and its cannula shell is locked in and sealed, then the obturator can be withdrawn to leave a smooth flow path beginning in the hub structure and continuing therein to a smooth blending with the proximal cannula region of the hub structure and continuing through the full length of the cannula to emerge at the distal end and in turn blend smoothly with the device's internal passage and then into the implanted catheter within the patient.

Other objects, features and advantages will be apparent from the following detailed description of preferred embodiments taken in conjunction with the accompanying drawings in which:

BRIEF DESCRIPTION OF THE DRAWINGS

FIGS. 1 and 2 are longitudinal sections of an improved access and lock device in cannula inserted and cannula removed situations.

FIGS. 1D, 1E, 1F, 1G, 1H illustrate certain details of the access device of FIGS. 1–2;

FIG. 3 is a top view of a pair of the strain relief element of the FIG. 1–2 device in an opened up position;

FIG. 3A is an end view of the structure shown in FIG. 3;

FIG. 4 shows the hub structure in axial section together with a portion of the lock device; and FIGS. 5, 5A and 5B show needle assembly details.

BRIEF DESCRIPTION OF PREFERRED EMBODIMENTS

Figure 1A:
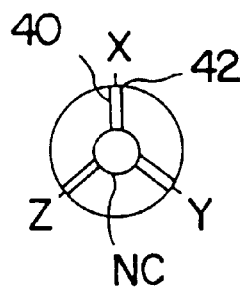
FIGS. 1A and 1B are cross-sectional views of one form of plug/blade lock assembly of the FIGS. 1–2 device in lock and unlock positions.

Referring now to FIGS. 1–2, each of the access device(s) 10, implantable just under the skin S of a patient, comprises a ceramic shell 12, a titanium connector 14 with an O-ring in groove 140 and segments 15 and a strain relief assembly 16. The connector 14 has an internal passage 18 along its central long axis A and a tube extension 20 configured to receive and hold a catheter end E. The shell 12 has an internal passage 22 along its central long axis which is a continuation of passage 18. An entrance portion 24 of the shell 12 has an opening along a sloped and concave front 26 so that a needle assembly N—including an obturator central portion and a surrounding metal sheath (needle cannula) NC—can be guided along the front and then pass through passage 22. A flexible valve 28 within the passage is easily pushed open by the needle assembly. A lock assembly 32 (see, also, FIGS. 4 and 5) within the shell 12 comprises a silicone rubber plug 34 with a hollow elongated passage 36 therein accommodating the inserted needle with some clearance and one or more (preferably three, but variable from one to ten) radial blades 40. Each blade has an axial-direction-tapered outer edge 42 tapering towards the shell entrance and the shell itself has a corresponding taper 44. Each blade also has an inner edge 46 which comprises one or more teeth preferably of shallow clearance angle ending in a point or small length contact with the cannula outer surface. Each blade has holes 50 allowing the plug to be continuous and retain the metal blades in relative positions to the rubber body and to each other.

Figure 1E:
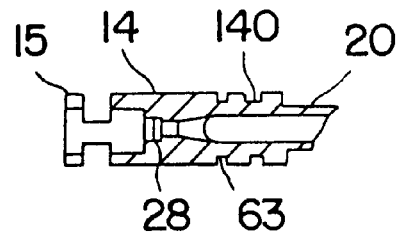
Figure 1B:
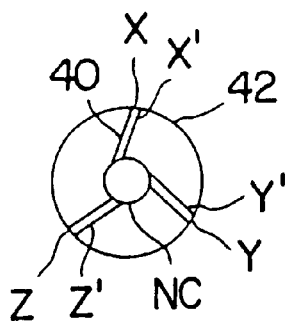
Figure 1F:
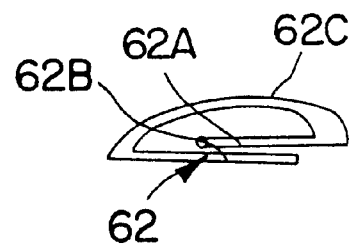

Comparing FIGS. 1A and 1B, both being cross-sections through the plug element of the access device of FIGS. 1–2, FIG. 1A shows blades 40 aligned on radial lines x, y, z and locking cannula NC while FIG. 1B shows the effect of twisting cannula NC so that the blades are aligned along non radial lines x', y', z' and the cannula is now unlocked and easily withdrawn. The twist of the cannula for removal can be clockwise or counter-clockwise (as in FIG. 1A). In either case the blades pivot about their outer edges 42. After the cannula is withdrawn the plug and blades return to the FIG. 1A position.

Figure 1C:
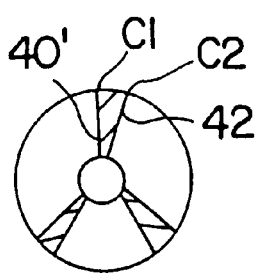
FIGS. 1C and 1H illustrates modifications of the blade configuration that are not mutually exclusive, FIG. 1H being a longitudinal section and 1C being a cross-section.
Figure 1G:
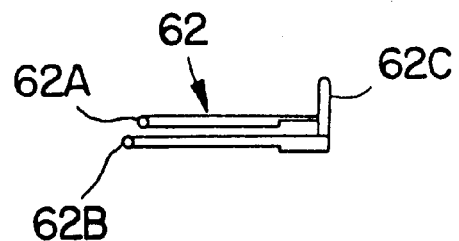
Figure 1D:
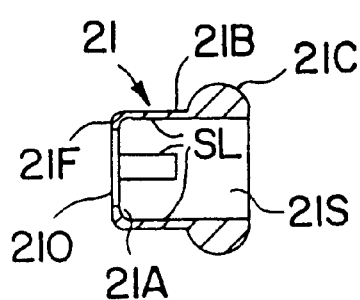
Figure 1H:
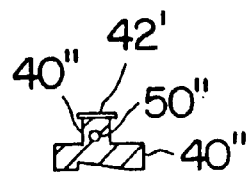

Other forms of the blades are shown in FIGS. 1C and 1H. In FIG. 1C, it is seen that blades 40' are cross section tapered to establish corners C1, C2 as pivot points for accommodating tilting of blades 40' from radial to non-radial alignment as cannula NC is twisted.

FIGS. 1D–1E shows the lock part 21 of FIGS. 1–2 as comprising a cup like structure of four legs (two shown at 21A, 21B ending in flanges 21F) separated by slots SL and having a base opening 21O, an interior surface 21S and a reinforced lip 21C. The flanges 21F seat in a groove 20F of transition connector piece 14 (see FIG. 2) to assure a good grip of catheter end E that passes over extension 20 of connector 14. An O-ring is provided in annular slot 140 (FIG. 2 and there is another slot 63).

FIG. 1H shows a form of blade 40 that has a limited length outer edge 42' compared to blade length as a whole. The blade 40 can be rectangular in cross section as in FIGS. 1A, 1B or tapered as in FIG. 1C. It is contained in the plug without a need for holes, but one such hole (50") can be provided optionally.

Flow in the Access Device(s)

Focusing now on FIGS. 1–2, it is seen that the internal passage can be very short, that a generally straight flow path is established and that the inner diameter of the cannula can be larger than is conventional. These factors allow the device to accommodate high fluid flow rates with low shear (i.e. lower than state of the art shear rates, generally, and short residence time at highest shear rate zones) and to limit other deleterious effects as to the fluid passing through.

The needle assembly (discussed in more detail in connection with FIGS. 5, 5A below) has an interior obturator nail and surrounding needle cannula sheath that can be of very thin wall construction. Thus for a standard cannula outer diameter of 0.072 in. an inner diameter of 0.0673 in. (compared to a standard of 0.064 in.) can be provided because of obturator reinforcement. That 0.0033 in. difference in inner diameter affords, approximately, a 20%+ decrease in flow resistance. The obturator also prevents a coring or cookie cutter effect that can arise from using a hollow needle for subcutaneous accessing.

The device also comprises the above mentioned duck-bill valve structure 28, seated between a retaining disk 52 (in turn held at an annular shoulder 54 of shell 12) and a ring 56 (or radial inserts instead of a ring), at the shell end, meeting the strain relief 16 which comprises a pair of clam shells 16A, 16B holding a long catheter end section straight to avoid bending, kinking or other strain sources at the proximal catheter end. The strain relief shown (FIGS. 3 and 3A) in open position (before closing about hinge F) can have flanges of a web form W, or other forms, and holes or hooks H for use in suturing (or otherwise securing) to subcutaneous tissue in fixed or movable fashion. The strain relief is a hinged assembly, shown open in FIG. 3, The duck-bill valve has upper and lower segments 60 (FIG. 1) that come together as indicated in FIG. 1B (the closed duckbill flaps being indicated at 60') when the cannula is withdrawn. This closure is urged by cantilever ends of a bent spring wire 62 (FIGS. 1F, 1G) with cantilevered spring ends 62A, 62B of a base segment 62C that passes around the duck-bill segments 60 along the outer edges of a volume 64 (FIGS. 1–2) within the transition piece 14 without interfering with the blood flow path. This valve structure as a whole leaves little room for blood accumulation or clotting when the needle is withdrawn and retraction of flaps to the storage spaces expels fluid therein back to the passage.

Strain Relief

FIG. 3 is a top view and FIG. 3A an end view of a pair of the FIG. 1–2 devices with the strain relief structure for two access and lock devices opened up. The strain relief structure has matched semi-cylindrical sections 16A, 16B (see also, FIGS. 1–2) for one device and a similar pair of semi-cylinder sections 17A, 17B for another device of a pair. All the sections are on a common plastic web W foldable along a fold line F (to match sections 16A/16B and 17A/17B) and having eyelets EY for suturing attachment to subcutaneous tissues. The numeral 18A' indicates half portions of passage(s) 18A (FIGS. 1–2). This fold out form of the strain relief allows insertion of two catheters C at 16B, 17B and tube extensions 20 (of connector pieces 14 of two devices 10) to fit into the catheter ends E. Parts 16A and 17A can then be folded over on to their complements 16B, 17B.

The web is shown axially coextensive with passages 18' but can in fact be made longer at one or more of the edges shown. Also a pivot zone is indicated at P/P' for attaching a pivot pad (that itself can be attached to subcutaneous tissue and the folded over web W and passages 18A and the catheter ends and devices 10 captured thereby can then all be movable under the skin about such pivot. Thus in sequential hemodialysis sessions a day or two apart, the ganged devices 10 can be pivoted to allow needle access at different skin puncture sites while other such sites heal.

Hub Structure

FIG. 4 shows a hub structure 100 associated with each lock device 10. The hub structure may have two involved parts 102, 104 of plastic, as shown, or metal or ceramic meeting at a surface 106 and as assembled by adhesives, solvent bonding or other means or cast a single piece. In any case there are three internal passages 108, 110, 112 provided, respectively, for the needle assembly, connection to a blood line ST from a dialysis machine and a control entry for the needle assembly that can hold a long extension of the obturator or an extension rod or linkage connected thereto (in either case with an operating handle H that allows axial pushing/pulling of the obturator. The needle cannula NC terminates in passage 108 and is bonded thereto. Thus rotating the hub structure 100 as a whole rotates the needle cannula for unlocking the cannula within the member 32 as described above in connection with FIGS. 1–2. Alternatively an inserted sleeve with dial access can provide a similar control. An insert 114 has a Y-passage therein connecting ends of passages 108, 110, 112 and with smooth internal flow path radii in the flow path section. Generally. passages 116 and 108, 110, 112 (and NC/OB as well as internal passages 22 of device 10) are of round form, preferably, but can be square or triangular or oval form or other shape.

Needle/Cannula

FIGS. 5 and 5A show an axial section of the distal end of the needle with assembly with the needle cannula (NC) having a needle cannula end NCE that is beveled inwardly to provide a cutting, annular edge rather than a blunt annular pushing surface and to blend with an obturator (OB) tip OBT. The end NCE also seats firmly on a corresponding cone within the passage 22 portion referred in transition connector 14 (FIG. 1E). The obturator tip has a distal end with multiple facets (preferably three) as shown in FIG. 5A backed by a collar region OBC or a greater number of facets providing a transition to annular form that blends smoothly with NCE. However, in a variant as indicated in FIG. 5B, a flat cutaway area CA can be provided and run down the length of the obturator at least to where it clears into passage 116 to relieve air pressure (if any) in passage 22 ahead of the obturator tip.

The obturator cutting for skin penetration is done along meeting lines of distal end facets rather than solely or primarily at the distal point. This avoids pain to the patient since the cut over a short length does not tear skin over a significant length. However, when the obturator point goes through the passage of the device, it does not cut, score or otherwise mar the internal wall of the passage or interiors of the locking and sealing components of the device which form part of the passage. The collar section OBC extending out of the cannula faceted in a larger number of facets than in the region of the point and at a larger diameter does not score of the internal passage of the device. Once the needle is fully inserted and its cannula shell is locked in and sealed, the obturator can be withdrawn to leave a smooth flow path beginning in the hub structure and continuing therein to a smooth blending with the proximal cannula region of the hub structure and continuing through the full length of the cannula to emerge at the distal end and in turn blend smoothly with the device internal passage and then into the implanted catheter within the patient.

Variants

There can be non-annular forms of the locking device. For example, the parts shown as annular pieces or arrays in FIGS. 1–2 can be part-annular. The locking blades can be of various other forms, e.g. blocks, balls, rollers. Springs or coil or leaf or other types can be used to assist locking or unlocking actions. The locking action can involve inscribing a cannula outer surface, holding it by friction or geometric blocking of a locking element with a rib or other protrusion on such surface. The duck-bill seal and/or its closing bias spring can be of various forms.

It will now be apparent to those skilled in the art that other embodiments, improvements, details, and uses can be made consistent with the letter and spirit of the foregoing disclosure and within the scope of this patent, which is limited only by the following claims, construed in accordance with the patent law, including the doctrine of equivalents.

What is claimed is:

1. In an access device for subcutaneous access for transfer of fluid into and/or out of a human or animal body and defining an internal passage therein and having a device entrance for access at one end by a cannula passing through the skin and at the other end by an implanted conduit such as a catheter, the improvement therein comprising:
    (a) locking structure within the device adjacent the internal passage and any cannula therein and restrained within the device,
    (b) means defining a shell structure surrounding the locking structure and having an internal surface adjacent to the locking structure,
    (c) means defining at least one essentially rigid blade within the shell spanning the gap between the surface of a cannula inserted in the passage and said internal shell surface, and
    (d) said internal shell surface being tapered toward the device entrance so that the beginning of inadvertent cannula withdrawal motion produces an increase in locking force against the at least one blade that in turn restrains cannula axial movement,
    the foregoing structure being constructed and arranged so that twisting the cannula pushes each blade from its locking alignment to an unlocking alignment to allow easy cannula withdrawal.

2. Device in accordance with claim 1 wherein three blades are provided.

3. Device in accordance with claim 1 wherein four or more blades are provided.

4. Device in accordance with any of claims 1 or 2 wherein the blades also have an external edge tapering down towards the entrance, corresponding to the taper of said shell internal surface.

5. Device in accordance with claim 1 and further comprising a flexible seal that is held out of the passage when the cannula is inserted and is urged into the passage to block it when the cannula is withdrawn.

6. Device in accordance with claim 5 wherein the flexible seal is in the form of a flexible multiple flap.

7. Device in accordance with claim 6 wherein a small pocket is provided for each flap when pushed aside by the cannula, such pockets being the only regions of the seal for fluid collection when the flaps block the entrance.

8. Device in accordance with claim 7 wherein wire springs are provided to urge the flaps into closing position.

9. Device in accordance with claim 6 wherein there are two flaps to form a duckbill seal.

10. Device in accordance with 6, or 7 wherein cantilever wire springs are provided to urge the flaps into closing position.

11. An access system for transfer of fluid into and/or out of a human or animal body, comprising:
    (a) at least one subcutaneously implantable access and lock device with an internal passage, the device being constructed and arranged with an internal body fluid conduit at one end of its internal passage and means to receive a cannula passing through the skin of said body at its other internal passage end and relatively lock the cannula therein or unlock it,
    (b) means defining needle assembly with a thin wall sheath or cannula and an internal obturator movable axially therein,
    (c) means defining a hub structure for use outside the body for establishing a fluid flow moving between an external conduit and said cannula for providing a passage for controlled positioning of said obturator,
    (d) the cannula and obturator being insertable into the access and lock device together and removable separately, whereby the assembled cannula and obturator can be passed through the skin from outside the body to reach the internal passage of the lock device and lock the cannula therein, and wherein the obturator can then be removed, and
    means for unlocking and removal of the cannula.

12. The system of claim 11 wherein a connected multiple of lock devices are provided in a form implantable together and in parallel.

13. The system of claim 12 wherein a strain relief for a catheter attached to each device is provided and such strain relief is constructed and arranged to act as a supporting structure for each device, said strain relief including a web enclosure that surrounds the device and the proximal end of said catheter to avoid catheter distortion while allowing said device to pivot under the skin.

14. The system of either of claims 11 or 12 wherein the access and lock device has separate lock and seal elements therein, the lock element being constructed and arranged to control locking/unlocking of the cannula relative to the device by cannula insertion and the seal element constructed and arranged to seal the passage when the cannula is withdrawn.

15. The system of claim 14 wherein the hub structure has a cannula locked into such hub structure so that hub structure rotation results in cannula rotation.

16. The system of either of claims 11 or 12 wherein said hub structure associated with an access and lock device has a cannula locked into such hub structure so that hub structure rotation results in cannula rotation.

17. In an access device for subcutaneous access for transfer of fluid into and/or out of a human or animal body and defining an internal passage therein for access at one end by a cannula passing through the skin and at the other end by an implanted conduit such as a catheter, the improvement therein comprising:
    (a) a sealing structure within the device adjacent the internal passage and any cannula therein with a movable portion of the sealing structure in a retracted position when a cannula is in the passage;
    (b) the movable portion being constructed and arranged to automatically block the passage as the cannula is withdrawn from the passage wherein the movable portion of the seal structure is flexible and in the form of flexible multiple flaps, said multiple flaps having two flaps to form a duckbill seal, and a small pocket is provided for each flap when pushed aside by the cannula, said pockets being the only regions of the seal for fluid collection when the flaps block the internal passage;

(c) the sealing structure providing substantially no volume unswept by flow through said access device internal passage other than a storage volume for the retracted movable portion that is filled by said portion upon retraction to thereby expel fluid, collected therein during sealing, back into the flow passage as the cannula is reinserted.

18. Device in accordance with claim 17 wherein wire springs are provided to urge the flaps into closing position.

19. In an access device for subcutaneous access for transfer of fluid into and/or out of a human or animal body and defining an internal passage therein for access at one end by a cannula passing through the skin and at the other end by a proximal end of an implanted conduit such as a catheter, and wherein strain relief is provided, said strain relief comprising a web enclosure that is capable of surrounding the access device and the proximal end of the catheter to avoid catheter distortion while allowing the access device to pivot under the skin.

20. A device in accordance with claim 19 wherein said strain relief web enclosure folds over said access device and may be unfolded to allow opening up for insertion of the device and catheter end.

21. A device as defined in claim 20 wherein said web enclosure encloses more than one access device.

22. Device in accordance with any of claims 19, 20 or 24 with the strain relief pivotable within the human or animal body to vary the passage access and location.

23. In an access device for an assembly to leave a streamlined flow passage from an external flow passage through a structure, a cannula having a distal end, an access device passage and a catheter subcutaneous access for transfer of fluid into and/or out of a human or animal body and defining an internal passage therein for access at one end by a cannula passing through the skin and at the other end by an implanted conduit such as a catheter, the improvement therein and further comprising:

a needle assembly comprising a thin walled cannula shell and an internal obturator rod, the rod having a distal end that protrudes out of the cannula distal end so that the assembly can penetrate the skin, guide an access end of the device and pass through the passage without scoring or otherwise marring passage defining walls, wherein said protruding end is of generally conical form, has a distal endmost section and next-to-endmost section (collar), the latter blending smoothly into a needle and the former providing the principal skin cutting portion in a way that penetrates skin without making long tears therein, wherein the protruding end is faceted with a first series of facets at said distal end and a second series of facets at the collar of greater number than the first series.

24. Device in accordance with any of claims 23 and further comprising an air escape passage along the needle assembly length.

25. Device in accordance with claim 24 wherein an elongated chordally cut-away section of the obturator provides such air escape passage within a round cannula interior.

26. Device in accordance with claim 23 wherein the device is ganged with a hub structure external to the human or animal body and the needle cannula shell is extendible from a cannula proximal end within the hub structure to within a subcutaneously implanted access device, an obturator extending through said hub structure via a second passageway and through said cannula, the hub structure having an internal flow passage blending smoothly with said second passageway at said cannula proximal end, the obturator being removable from the needle assembly to leave a streamlined flow passage from an external flow passage through the hub structure, cannula, access device passage and catheter.

* * * * *